(12) United States Patent
Koder et al.

(10) Patent No.: US 8,901,069 B2
(45) Date of Patent: Dec. 2, 2014

(54) PROTEIN MATRIX FOR LIGHT-INITIATED ELECTRON TRANSFER

(75) Inventors: Ronald Lee Koder, Brooklyn, NY (US); Andrew Colin Mutter, Bronx, NY (US)

(73) Assignee: Research Foundation of The City University of New York, New York, NY (US)

( * ) Notice: Subject to any disclaimer, the term of this patent is extended or adjusted under 35 U.S.C. 154(b) by 241 days.

(21) Appl. No.: 13/262,085

(22) PCT Filed: Apr. 19, 2010

(86) PCT No.: PCT/US2010/031621
§ 371 (c)(1),
(2), (4) Date: Oct. 26, 2011

(87) PCT Pub. No.: WO2010/121259
PCT Pub. Date: Oct. 21, 2010

(65) Prior Publication Data
US 2012/0034671 A1 Feb. 9, 2012

Related U.S. Application Data

(60) Provisional application No. 61/212,878, filed on Apr. 17, 2009.

(51) Int. Cl.
*C07K 14/00* (2006.01)
*C07K 14/795* (2006.01)

(52) U.S. Cl.
CPC .................................. *C07K 14/795* (2013.01)
USPC .............................................. 514/2; 530/300

(58) Field of Classification Search
None
See application file for complete search history.

(56) References Cited

U.S. PATENT DOCUMENTS

2005/0255515 A1 11/2005 Roitman et al.

OTHER PUBLICATIONS

McDermott et al., "Crystal structure of an integral membrane light-harvesting complex from photosynthetic bacteria", Nature 374, 517-521, Apr. 6, 1995.*
Hasharoni et al., "Radical Pair and Triplet State Dynamics of a Photosynthetic Reaction-Center Model Embedded in Isotropic Media and Liquid Crystals", J. Am. Chem. Soc. 118, pp. 10228-10235 (1996).
Faver et al., "Reductant-Dependent Electron Distribution Among Redox sites of Laccase", Proc. Natl. Acad. Sci, vol. 75, No. 11, pp. 5245-5249 (1978).
Matsushita et al., "A Tightly Bound Quinone Functions in the Ubiquinone Reaction Sites of Quinoprotein Alcohol Dehydrogenase of an Acetic Acid Bacterium, Gluconobacter Suboxydans", Biosci. Biotechnol. Biochem., 72 (10), pp. 2723-2731 (2008).
Dementin et all., "Changing the Ligation of the Distal [4Fe4S] Cluster in NiFe Hydrogenae Impairs Inter-and Intramolecular Electron Transfers", J. Am. Chem. Soc., 128, pp. 5209-5218 (2006).
Hu et al. "Construction of Artificial Photosynthetic Reaction Centers on a Protein Surface: Vectorial, Multistep, and Proton-Coupled Electron Transfer for Long-Lived Charge Separation", J. Am. Chem. Soc. 122, pp. 241-253 (2000).
Zhang et al. "Photoinduced multi-electron transfer in the Dn-A system consisting of multi-phthalocyanines linked to one carbon nanotube"; Phys. Chem. Chem. Phys. (2009) 11, 3566-3572 (published online Mar. 13, 2009), entire document.
Kodis et al., "Energy and Photoinduced Electrono Transfer in a Wheel-Shaped Artificial Photosynthetic Antenna-Reaction Center Complex", J. Am Chem. Soc (2006) 128; 1818-1827, entire document.
Straight et al.. "Self-regulation of photoinduced electron transfer by a molecular nonlinear transducer"; Nature Nanotechnology, vol. 3, (2008), pp. 280-283, entire document.
Wieckowska et al., "A novel polynuclear donor complex based on helical peptides with aligned electroactive moieties"; Chemical Physics Letters vol. 350, Issued 5-6, Dec. 28, 2001; pp. 447-452, abstract only.
Lang et al., "Long-Range Electron Transfer in Rigid 310-Helical Oligopeptides Containing Redox Cyclic a-Amino Acids", Photochemistry and Photobiology vol. 70; Issue 4; pp. 579-584. Published online Jan. 2, 2008, abstract only.
Striplin et al., "Solvent Dependence of Intramolecular Electron Transfer in a Helical Oligoproline Assembly"; J. Am. Chem. Soc. (2004); 126 (16); pp. 5282-5291. esp: abstract.
Alstrum-Acevedo et al., "Chemical Approaches to Artificial Photosynthesis. 2", Inorg. Chem. (2005); 44, 6802-6827; esp p. 6824-6825 Section entitled "Oligoprolines", Fig 13.
Fukuzumi, "Bioinspired Electron-Transfer Systems and Applications", Bull. Chem. Soc. Jpn. vol. 79, No. 2, 177-195 (2006), entire document.
Koder et al., "Intelligent design: the de novo engineering of proteins with specified functions", Dalton Trans (2006) 3045-3051, entire document.
Moore et al., "Bio-inspired constructs for sustainable energy production and use," L'actualite Chimique (2007)—No. 308-309, pp. 50-56, entire document.
Gould et al., "Artificial Photosynthetic Reaction Centers with Prophyrins as Primary Electron Acceptors", J. Phys. Chem. B (2004) 108, 10566-10580, entire document.
Herrero et al., "Artificial systems related to light driven electron transfer processes in PSII," Coordination Chemistry Reviews 252 (2008) 456-468, entire document.
Noy et al., "Design and engineering of photosynthetic light-harvesting and electron transfer using length, time, and energy scales", Biochimica et Biophysica Acta 1757 (2006) 90-105, entire document.

* cited by examiner

*Primary Examiner* — Anand Desai

(74) *Attorney, Agent, or Firm* — Hoffmann & Baron, LLP

(57) ABSTRACT

The present invention provides selective modification of polypeptide sequences with electron transfer moieties. The resulting polypeptide assemblies represent a novel class of electron transfer complexes that are capable of transferring electrons over very long distances at fast rates. These complexes possess unique structural features which enable the production of bioconductors and photoactive probes.

28 Claims, 4 Drawing Sheets

SEQUENCE LISTING

```
<160> NUMBER OF SEQ ID NOS: 17

<210> SEQ ID NO 1
<211> LENGTH: 132
<212> TYPE: PRT
<213> ORGANISM: Artificial Sequence
<220> FEATURE:
<223> OTHER INFORMATION: Chemical synthesis

<400> SEQUENCE: 1

Gly Glu Ile Trp Lys Gln His Glu Asp Ala Leu Gln Lys Phe Glu Glu
1               5                  10                  15

Ala Leu Asn Gln Phe Glu Asp Leu Lys Gln Leu Gly Gly Ser Gly Cys
            20                  25                  30

Gly Ser Gly Gly Glu Ile Trp Lys Gln His Glu Asp Ala Leu Gln Lys
        35                  40                  45

Phe Glu Glu Ala Leu Asn Gln Phe Glu Asp Leu Lys Gln Leu Gly Gly
    50                  55                  60

Ser Gly Ser Gly Ser Gly Gly Glu Ile Trp Lys Gln His Glu Asp Ala
65                  70                  75                  80
```

-continued

Leu Gln Lys Phe Glu Glu Ala Leu Asn Gln Phe Glu Asp Leu Lys Gln
                85                  90                  95

Leu Gly Gly Ser Gly Cys Gly Ser Gly Gly Glu Ile Trp Lys Gln His
            100                 105                 110

Glu Asp Ala Leu Gln Lys Phe Glu Glu Ala Leu Asn Gln Phe Glu Asp
        115                 120                 125

Leu Lys Gln Leu
    130

<210> SEQ ID NO 2
<211> LENGTH: 133
<212> TYPE: PRT
<213> ORGANISM: Artificial Sequence
<220> FEATURE:
<223> OTHER INFORMATION: Chemical synthesis

<400> SEQUENCE: 2

Gly Ser Glu Ile Trp Lys Gln His Glu Asp Ala Leu Gln Lys Phe Glu
1               5                   10                  15

Glu Ala Leu Asn Gln Phe Glu Asp Leu Lys Gln Leu Gly Gly Ser Asn
            20                  25                  30

Ser Gly Ser Gly Gly Glu Ile Trp Lys Gln His Glu Asp Ala Leu Gln
        35                  40                  45

Lys Phe Glu Glu Ala Leu Asn Gln Phe Glu Asp Leu Lys Gln Leu Gly
    50                  55                  60

Gly Ser Ser Thr Gly Ser Gly Gly Glu Ile Trp Lys Gln Phe Glu Asp
65                  70                  75                  80

Ala Leu Gln Lys Phe Glu Glu Ala Leu Asn Gln Phe Glu Asp Leu Lys
                85                  90                  95

Gln Leu Gly Gly Ser Ser Gly Ser Gly Gly Glu Ile Trp Lys Gln
            100                 105                 110

His Glu Asp Ala Leu Gln Lys Phe Glu Glu Ala Leu Asn Gln Phe Glu
        115                 120                 125

Asp Leu Lys Gln Leu
    130

<210> SEQ ID NO 3
<211> LENGTH: 137
<212> TYPE: PRT
<213> ORGANISM: Artificial Sequence
<220> FEATURE:
<223> OTHER INFORMATION: Chemical synthesis

<400> SEQUENCE: 3

Gly Ser Pro Gln Glu Ala Gln Gln Thr Ala Gln Glu Ala Gln Gln Ala
1               5                   10                  15

Leu Gln Glu His Gln Gln Ala Val Gln Ala Ala Gln Leu Asn Glu
            20                  25                  30

Leu Asp Ala Ser Gln Glu His Gln Gln Ala Thr Gln Ala Ala Gln Gln
        35                  40                  45

Thr Ala Gln Lys Ala Gln Gln Ala Leu Gln Lys His Met Ala Thr Gly
    50                  55                  60

Leu Tyr Ser Gly Ser Tyr Arg Ser Pro Leu Val Thr Leu Trp Asn Val
65                  70                  75                  80

Ala Gln Glu Ala Gln Gln Ala Leu Gln Glu Leu Gln Gln Ala Thr Gln
                85                  90                  95

Ala Ala Gln Gln Leu Asn Glu Leu Asp Ala Leu Gln Glu His Gln Gln

```
                      100                 105                 110

Ala Ser Gln Ala Ala Gln Gln Thr Ala Gln Lys Ala Gln Gln Ala Leu
        115                 120                 125

Gln Lys His Gln Gln Ala Ser Gln Lys
    130                 135

<210> SEQ ID NO 4
<211> LENGTH: 135
<212> TYPE: PRT
<213> ORGANISM: Artificial Sequence
<220> FEATURE:
<223> OTHER INFORMATION: Chemical synthesis

<400> SEQUENCE: 4

Gly Ser Pro Gln Glu Ala Gln Gln Thr Ala Gln Glu Ala Gln Gln Ala
1               5                   10                  15

Leu Gln Glu His Gln Gln Ala Val Gln Ala Ala Gln Gln Leu Asn Glu
                20                  25                  30

Leu Asp Ala Ser Gln Glu His Gln Gln Ala Thr Gln Ala Ala Gln Gln
            35                  40                  45

Thr Ala Gln Lys Ala Gln Gln Ala Leu Gln Lys His Met Ala Thr Gly
50                  55                  60

Gly Gly Ser Gly Gly Ser Pro Leu Val Thr Leu Trp Asn Val Ala Gln
65                  70                  75                  80

Glu Ala Gln Gln Ala Leu Gln Glu Leu Gln Ala Thr Gln Ala Ala
                85                  90                  95

Gln Gln Leu Asn Glu Leu Asp Ala Leu Gln Glu His Gln Gln Ala Ser
            100                 105                 110

Gln Ala Ala Gln Gln Thr Ala Gln Lys Ala Gln Gln Ala Leu Gln Lys
        115                 120                 125

His Gln Gln Ala Ser Gln Lys
    130                 135

<210> SEQ ID NO 5
<211> LENGTH: 30
<212> TYPE: PRT
<213> ORGANISM: Artificial Sequence
<220> FEATURE:
<223> OTHER INFORMATION: Chemical synthesis

<400> SEQUENCE: 5

Cys Gly Gly Gly Glu Ile Trp Lys Gln His Glu Glu Ala Leu Lys Lys
1               5                   10                  15

Phe Glu Glu Ala Leu Lys Gln Phe Glu Glu Leu Lys Lys Leu
                20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Chemical synthesis

<400> SEQUENCE: 6

Cys Gly Gly Gly Glu Ile Trp Lys Gln His Glu Asp Ala Leu Gln Lys
1               5                   10                  15

Phe Glu Glu Ala Leu Asn Gln Phe Glu Asp Leu Lys Gln Leu
                20                  25                  30

<210> SEQ ID NO 7
```

<211> LENGTH: 62
<212> TYPE: PRT
<213> ORGANISM: Artificial Sequence
<220> FEATURE:
<223> OTHER INFORMATION: Chemical synthesis

<400> SEQUENCE: 7

Gly Glu Ile Trp Lys Gln His Glu Asp Ala Leu Gln Lys Phe Glu Glu
1               5                   10                  15

Ala Leu Asn Gln Phe Glu Asp Leu Lys Gln Leu Gly Gly Ser Gly Cys
            20                  25                  30

Gly Ser Gly Gly Glu Ile Trp Lys Gln His Glu Asp Ala Leu Gln Lys
        35                  40                  45

Phe Glu Glu Ala Leu Asn Gln Phe Glu Asp Leu Lys Gln Leu
    50                  55                  60

<210> SEQ ID NO 8
<211> LENGTH: 62
<212> TYPE: PRT
<213> ORGANISM: Artificial Sequence
<220> FEATURE:
<223> OTHER INFORMATION: Chemical synthesis

<400> SEQUENCE: 8

Gly Glu Ile Trp Lys Gln His Glu Asp Ala Leu Gln Lys Phe Glu Glu
1               5                   10                  15

Ala Leu Asn Gln Phe Glu Asp Leu Lys Gln Leu Gly Gly Ser Gly Cys
            20                  25                  30

Gly Ser Gly Gly Glu Ile Trp Lys Gln His Ala Asp Ala Leu Gln Lys
        35                  40                  45

Phe Ala Glu Ala Leu Asn Gln Phe Ala Asp Leu Lys Gln Leu
    50                  55                  60

<210> SEQ ID NO 9
<211> LENGTH: 16
<212> TYPE: PRT
<213> ORGANISM: Artificial Sequence
<220> FEATURE:
<223> OTHER INFORMATION: Chemical synthesis
<220> FEATURE:
<221> NAME/KEY: VARIANT
<222> LOCATION: 2, 3, 4, 6, 7, 10, 11
<223> OTHER INFORMATION: Xaa = Any Amino Acid

<400> SEQUENCE: 9

Ile Xaa Xaa Xaa Leu Xaa Xaa His Ala Xaa Xaa Ala Ile Ile Ile Phe
1               5                   10                  15

<210> SEQ ID NO 10
<211> LENGTH: 62
<212> TYPE: PRT
<213> ORGANISM: Artificial Sequence
<220> FEATURE:
<223> OTHER INFORMATION: Chemical synthesis

<400> SEQUENCE: 10

Gly Glu Ile Trp Lys Gln His Glu Asp Ala Leu Gln Lys Phe Glu Glu
1               5                   10                  15

Ala Leu Asn Gln Phe Glu Asp Leu Lys Gln Leu Gly Gly Ser Gly Cys
            20                  25                  30

Gly Ser Gly Gly Glu Ile Leu Lys Gln His Ala Asp Ala Ala Gln Lys
        35                  40                  45

Ile Phe Glu Ala Leu Asn Gln Phe Glu Asp Leu Lys Gln Leu

```
            50                  55                  60
```

<210> SEQ ID NO 11
<211> LENGTH: 62
<212> TYPE: PRT
<213> ORGANISM: Artificial Sequence
<220> FEATURE:
<223> OTHER INFORMATION: Chemical synthesis

<400> SEQUENCE: 11

```
Gly Glu Ile Trp Lys Gln His Glu Asp Ala Leu Gln Lys Phe Glu Glu
 1               5                  10                  15

Ala Leu Asn Gln Phe Glu Asp Leu Lys Gln Leu Gly Gly Ser Gly Cys
            20                  25                  30

Gly Ser Gly Gly Glu Ile Trp Lys Gln Phe Glu Asp Ala Leu Gln Lys
        35                  40                  45

Phe Glu Glu Ala Leu Asn Gln Phe Glu Asp Leu Lys Gln Leu
    50                  55                  60
```

<210> SEQ ID NO 12
<211> LENGTH: 6
<212> TYPE: PRT
<213> ORGANISM: Artificial Sequence
<220> FEATURE:
<223> OTHER INFORMATION: Chemical synthesis

<400> SEQUENCE: 12

```
Gly Ala Thr Asn Gly Gly
 1               5
```

<210> SEQ ID NO 13
<211> LENGTH: 8
<212> TYPE: PRT
<213> ORGANISM: Artificial Sequence
<220> FEATURE:
<223> OTHER INFORMATION: Chemical synthesis

<400> SEQUENCE: 13

```
Gly Ala Thr Asn Thr Asn Gly Gly
 1               5
```

<210> SEQ ID NO 14
<211> LENGTH: 10
<212> TYPE: PRT
<213> ORGANISM: Artificial Sequence
<220> FEATURE:
<223> OTHER INFORMATION: Chemical synthesis

<400> SEQUENCE: 14

```
Gly Ala Thr Asn Thr Asn Ala Arg Gly Gly
 1               5                  10
```

<210> SEQ ID NO 15
<211> LENGTH: 13
<212> TYPE: PRT
<213> ORGANISM: Artificial Sequence
<220> FEATURE:
<223> OTHER INFORMATION: Chemical synthesis
<220> FEATURE:
<221> NAME/KEY: VARIANT
<222> LOCATION: 2, 3, 6, 10, 11
<223> OTHER INFORMATION: Xaa = Any Amino Acid

<400> SEQUENCE: 15

```
Ala Xaa Xaa Ala Cys Xaa Ala Cys His Xaa Xaa Leu Ala
 1               5                  10
```

```
<210> SEQ ID NO 16
<211> LENGTH: 5
<212> TYPE: PRT
<213> ORGANISM: Artificial Sequence
<220> FEATURE:
<223> OTHER INFORMATION: Chemical synthesis
<220> FEATURE:
<221> NAME/KEY: VARIANT
<222> LOCATION: 2, 3
<223> OTHER INFORMATION: Xaa = Any Amino Acid

<400> SEQUENCE: 16

Cys Xaa Xaa Cys His
 1               5

<210> SEQ ID NO 17
<211> LENGTH: 9
<212> TYPE: PRT
<213> ORGANISM: Artificial Sequence
<220> FEATURE:
<223> OTHER INFORMATION: Chemical synthesis

<400> SEQUENCE: 17

Gly Gly Ser Gly Ser Gly Ser Gly Gly
 1               5
```

PROTEIN MATRIX FOR LIGHT-INITIATED ELECTRON TRANSFER

CROSS REFERENCE TO PRIOR APPLICATIONS

This is a U.S. National Phase application under 35 U.S.C. §371 of International Patent Application No. PCT/US2010/031621, filed Apr. 19, 2010, and claims the benefit of U.S. Patent Application No. 61/212,878, filed Apr. 17, 2009 both of which are incorporated by reference herein. The International Application published in the English language on Oct. 21, 2010 as WO 2010/121259 under PCT Article 21(2).

GOVERNMENT INTEREST STATEMENT

Research and development leading to invention(s) described herein was supported, at least in part, under government Contract No. MCB-920448 awarded by the National Science Foundation. The United States government may have certain rights to the invention(s) pursuant to the terms of those contracts.

REFERENCE TO SEQUENCE LISTING

A Sequence Listing is submitted herewith, pursuant to 37 C.F.R. 1.821(c), as an ASCII compliant text file named "SEQLST.txt," which was created on Apr. 19, 2010 and has a size of 9,941 bytes. The content of the aforementioned "SequenceListing.txt" file is hereby incorporated by reference in its entirety.

FIELD OF THE INVENTION

This invention relates to the design of de novo electron transport polypeptides and to uses of these polypeptides, for example, as photoactive probes.

BACKGROUND OF THE INVENTION

The development of renewable and environmentally benign energy sources has emerged as one of the most pressing challenges of the 21$^{st}$ century. It has been estimated that increases in world population coupled with the rise of emerging economies will produce an increase in energy consumption from 13 TW today to 30 TW by 2050 (Lewis et al., *Proceedings of the National Academy of Sciences* (2006) 103:15729). Given that 86% of this energy comes from fossil fuels, and that $CO_2$ levels are currently the highest they have been for the past 650,000 years, it is clear that the burn rate that will be needed to sustain future energy requirements is unacceptable (Herrero et al., *Coordination Chemistry Reviews* (2008) 252:456-468).

Natural photosynthesis converts solar energy into chemical energy in a non-toxic and highly efficient manner, and has thus been studied for decades as a model for the creation of photo-induced renewable energy devices. During photosynthesis, absorption of light by phototrophic organisms initiates a series of electron transfer reactions that lead to the production of carbohydrates upon reduction of $CO_2$ and the oxidation of $H_2O$ to $O_2$. The photosynthetic process can be described by the following formulae:

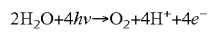

$$2H_2O + 4h\nu \rightarrow O_2 + 4H^+ + 4e^-$$

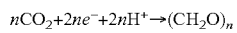

$$nCO_2 + 2ne^- + 2nH^+ \rightarrow (CH_2O)_n$$

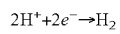

$$2H^+ + 2e^- \rightarrow H_2$$

The photosynthetic protein apparatus, which is a complex array of several membrane-bound proteins, self-assembles, absorbs most of the solar spectrum, and has a quantum efficiency of greater than 98% conversion of photon energy to the desired reaction products. Artificial photosynthesis thus aims to harness energy from electron transfer events to drive the production of high energetic fuels such as $H_2$ and reduced forms of carbon (Hay et al., *Proceedings of the National Academy of Sciences* (2004) 101:17675-17680).

Bio-inspired systems linking organic molecules to synthetic matrix scaffolds have strived to recreate individual elements of the photosynthetic apparatus (Fukuzumi et al., *Bulletin Of The Chemical Society Of Japan* (2006) 79:177-195; Kodis, G., Terazono et al., *J Am Chem Soc* (2006) 128: 1818-1827). These "integrated modular assemblies" have provided a basis for constructing molecular devices fashioned on nanoscale materials which position the active elements at fixed distances to transform photonic energy into vectorial electron transfer (Alstrum-Acevedo et al., *Inorganic Chemistry* (2005) 44:6802-6827; Meyer, et al. *Accounts Of Chemical Research* (1989) 22:163-170). However, the synthetic-based systems that have been constructed to date are expensive to prepare, synthetically challenging, and their production is often damaging to the environment (Coakley et al., *Chemistry Of Materials* (2004) 16:4533-4542). For these reasons, the prior art constructs are not feasible for commercial application.

Hence there is a pressing need for a simple, robust solar energy conversion device with the scale and complexity of natural systems, such as the photosynthetic reaction center, that can be constructed in an efficient, environmentally friendly, and cost effective manner.

SUMMARY OF THE INVENTION

An object of the invention is to provide at least a partial solution to the above-described problems and/or disadvantages in the prior art by providing a protein-based photovoltaic construct that is "green," robust, has high light conversion and efficiency, and is ready for integration into more complex assemblies.

Accordingly, a first embodiment of the present invention is directed to an isolated polypeptide capable of binding at least two electron transfer moieties, wherein the electron transfer moieties are arranged so that electron transfer can occur between at least two electron transfer moieties.

A second embodiment of the present invention is directed to an isolated polypeptide capable of binding at least three electron transfer moieties selected from an electron donor, a primary electron donor, and an electron acceptor, wherein the primary electron donor is positioned between the electron donor and the electron acceptor, and wherein the electron transfer moieties are arranged so that electron transfer can occur between each of the electron transfer moieties.

A third embodiment of the present invention is directed to a photovoltaic assembly comprising a charge separation domain covalently linked to a matrix, wherein the charge separation domain comprises an isolated polypeptide capable of binding at least three electron transfer moieties selected from an electron donor, a primary electron donor, and an electron acceptor, wherein the primary electron donor is positioned between the electron donor and the electron acceptor, and wherein the electron transfer moieties are arranged so that electron transfer can occur between each of the electron transfer moieties.

Additional advantages, objects, and features of the invention will be set forth in part in the description which follows

BRIEF DESCRIPTION OF THE DRAWINGS

Non-limiting and non-exhaustive embodiments of the present invention are described with reference to the following drawings. For a better understanding of the present invention, reference will be made to the following Detailed Description, which is to be read in association with the accompanying drawings, wherein:

FIG. 6B shows stopped-flow analysis of carbon monoxide binding to prereduced HP-7 (SEQ ID NO: 7) and CC-10 (SEQ ID NO: 10). Laser flash-photolysis kinetics analysis of HP-7 (SEQ ID NO: 7) is depicted in FIG. 6C. Pentagons represent histidines lying on each helix.

DETAILED DESCRIPTION

Figure 1:
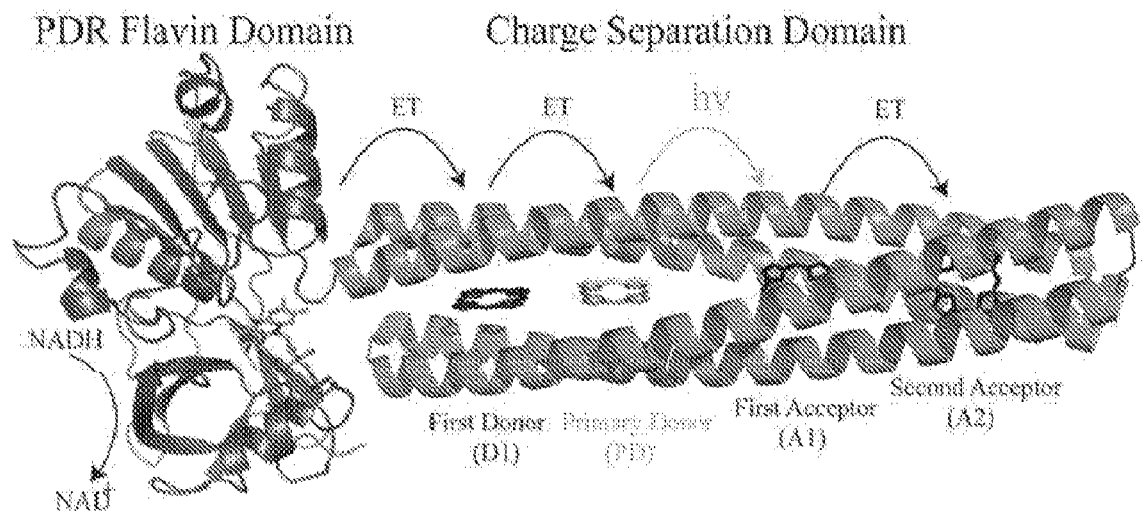
FIG. 1 is a schematic showing an exemplary chimeric charge separation construct comprising a first electron donor (D1), a primary electron donor (PD), a first electron acceptor (A1) and a second electron acceptor (A2). The charge separation chimera consists of a phthalate dioxygenase reductase (PDR) Flavin domain and a charge separation domain.

It is understood that the invention(s) described herein is (are) not limited to the particular methodologies, protocols, cell lines, vectors, polypeptides, and reagents described, as these may vary. For example, polypeptide sequences of this invention include, variant polypeptides; i.e. polypeptides which may differ in amino acid sequence by one or more substitutions, additions, deletions, truncations which may be present in any combination. It is also to be understood that the terminology used herein is for the purpose of describing particular embodiments only, and is not intended to limit the scope of the present invention. Rather, the invention will be limited only by the appended claims and any equivalents to which they are entitled.

Unless defined otherwise, all technical and scientific terms used herein have the same meanings as commonly understood by one of ordinary skill in the art to which this invention belongs. Any methods and materials similar or equivalent to those described herein can be used in the practice or testing of the present invention. However, the methods, devices, and materials described herein are generally prepared. All publications, including all patents, patent applications, and other patent and non-patent publications cited or mentioned herein are incorporated herein by reference for at least the purposes that they are cited; including, for example, for the disclosure or descriptions of methods and materials (e.g., proteins and/or other polypeptides, vectors, reagents, etc.) which may be used in the invention. Nothing herein is to be construed as an admission that a publication or other reference (including any reference cited in the "Background of the Invention" section alone) is prior art to the invention or that the invention is not entitled to antedate such disclosure, for example, by virtue of prior invention.

The skilled artisan will appreciate that the numerical values presented herein are approximate values. Generally, unless otherwise indicated, terms such as "about" and "approximately" include within 20% of the values indicated, more preferably within 10%, and even more preferably within 5%.

The present invention provides selective modification of polypeptide sequences with electron transfer moieties. The resulting polypeptide assemblies represent a novel class of electron transfer complexes that are capable of transferring electrons over very long distances at fast rates.

In one embodiment, the invention provides an isolated polypeptide capable of binding at least three electron transfer moieties selected from an electron donor, a primary electron donor, and an electron acceptor, wherein the primary electron donor is positioned between the electron donor and the electron acceptor, and wherein the electron transfer moieties are arranged so that electron transfer can occur between at least two electron transfer moieties.

Unless otherwise stated, the term "polypeptide" or "protein," or grammatical equivalents thereof, have the same meaning and refers to a peptide comprising two or more amino acids. The polypeptides of the present invention can encompass naturally occurring proteins, non-natural artificial proteins, as well as those which are recombinantly or synthetically produced. The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, for example, an α-carbon that is bound to a hydrogen, a carboxyl group, an amino group, and an R group. Such analogs may have modified R groups (for example, norleucine)

or may have modified peptide backbones, while still retaining the same basic chemical structure as a naturally occurring amino acid.

Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

In one embodiment, the polypeptide of the invention comprises about 2 to about 1000 amino acid residues. In another embodiment, the polypeptide comprises, about 15 to about 700, or 20 to about 500 or about 25 to about 250, or about 50 to 200, or about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, or 200 amino acid residues.

In a preferred embodiment, a polypeptide of the invention may be a multimer polypeptide, i.e., a polypeptide comprising a plurality of polypeptide chains and having at least one amino acid sequence that may be the same or different from the amino acid sequence of at least one other polypeptide monomer. Preferred polypeptide multimers are dimers and tetramers having two and four polypeptide chains, respectively. The dimer or tetramer polypeptides may be homodimers or homotetramers, respectively, having polypeptide chains that are identical to the other polypeptide chains in the homodimer or homotetramer. Alternatively, the dimer or tetramer polypeptides may be heterodimers or heterotetramers, respectively, having polypeptide chains that are different from the other polypeptide chains in the heterodimer or heterotetramer.

In another preferred embodiment, a polypeptide of the invention is a monomer, i.e., a polypeptide having a single polypeptide chain.

In another embodiment, the polypeptide of the invention is a non-natural protein, i.e., an "artificial" protein that does not naturally exist in nature.

The terms "electron donor," electron acceptor," and "electron transfer moieties," or grammatical equivalents thereof, refer to molecules capable of electron transfer under certain conditions. The primary electron donor preferably functions in the polypeptide by donating an electron to an electron acceptor. The electron acceptor preferably functions by accepting an electron from an electron donor. In one embodiment of the invention, the electron donor donates an electron to the primary electron donor. It is to be understood that electron transfer and acceptor capabilities are relative, that is, a molecule which can lose an electron under certain experimental conditions will be able to accept an electron under different experimental conditions. Those skilled in the art of electron transfer compounds will be familiar with and be able to utilize a number of such compounds in the present invention. Preferred electron transfer moieties include, but are not limited to, metal complexes, including transition metal complexes, organic electron transfer moieties, and electrodes.

In one embodiment of the invention, the electron transfer moieties are transition metal complexes. Transition metals are those whose atoms have an incomplete d shell of electrons. Suitable transition metals for use in the invention include, but are not limited to, scandium (Sc) cadmium, ytterbium (Y), titanium (Ti), zirconium (Zr), vanadium (V), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), (Ni), palladium (Pd), platinum (Pt), copper (Cu), silver (Ag), and gold (Au). Other suitable metals include, but are not limited to, zinc (Zn), cadmium (Cd), magnesium, (Mg), or any metal from the periodic table that is capable of forming a metal complex. Preferred metals are zinc, iron, ruthenium, and osmium. Particularly preferred metals are zinc and iron.

The metals may be complexed with a variety of ligands to form suitable metal complexes, as is well known in the art. Suitable ligands include, but are not limited to, $NH_2$; pyridine; pyrazine; corroles, chlorophylls, chlorins, isonicotinamide; imidazole; bipyridine, and substituted derivative of bipyridine; phenanthrolines, and substituted derivatives of phenanthrolines such as 4,7-dimethylphenanthroline; dipyridophenazine; 1,4,5,8,9,12-hexaazatriphenylene; 9,10-phenanthrenequinone diimine; 1,4,5,8-tetraazaphenanthrene; 1,4,8,11-tetra-azacyclotetradecane; diaminopyridine; pyrene; buckminsterfullerene; and porphyrins, and substituted derivatives of the porphyrin family such as phthalocyanine, and derivatives of phthalocyanine such as napthalocyanines.

Preferred metal complexes for use in the invention include, but are not limited to, Zinc(II) phthalocyanines (ZnPCs), and analogs thereof; other metal-bound porphyrins such as ferric heme, chlorophyll, corphins, and cobalamin; 2-iron-2-sulfur and 4-iron-4-sulfur clusters; and ferrocenes. Zinc(II) phthalocyanines and ferric heme are particularly preferred metal complexes for use in the invention.

In particular, phthalocyanines have long been proposed as ideal molecules to act as primary donor cofactors in artificial light-powered devices due to their chemical robustness (relative to chlorophyll and porphyrin derivatives), ease of synthesis and long wavelength action spectrum (De la Tone et al., *Chemical Communications* (2007) 2000-2015; Rawling et al., *Coordination Chemistry Reviews* (2007) 251:1128-1157). Phthalocyanines exhibit high molar absorptivity B bands, with maxima at near infrared wavelengths of 650 nm and above, and are thus ideal for solar energy conversion. The chemical structure for zinc phthalocyanine is depicted below:

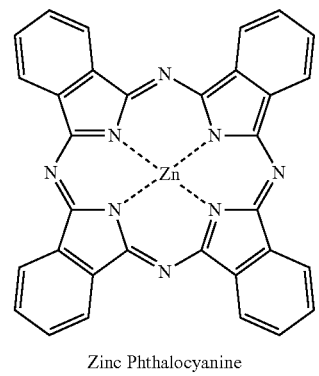

Zinc Phthalocyanine

In spite of their advantages, phthalocyanines have had very little translation into practical systems because they are highly susceptible to self-association and form stacked, columnar aggregates with poor photophysical properties (Schutte et al., *Journal Of Physical Chemistry* (1993) 97:6069-6073). Efforts to isolate monomeric forms of phthalocyanines, i.e., referenced in the art as "splendid isolation" (Brewis et al., *Journal Of Porphyrins And Phthalocyanines* (2000) 4:460-464), have failed to inhibit the progressive accumulation of stacked phthalocyanines because the cofacial stacking interaction is highly thermodynamically stable. Thus an object of the present invention is to provide a polypeptide assembly which will bind phthalocyanines in isolation so that the advantageous features of the monomeric electron donor can be exploited.

In addition to metal complexes, other organic electron donors and acceptors may be covalently attached to a polypeptide for use in the invention. These organic molecules include, but are not limited to, flavin mononucleotide, flavin adenine dinucleotide, riboflavin, xanthene dyes, azine dyes, acridine orange, N,N'-dimethyl-2,7-diazapyrenium dichloride, methylviologen, ethidium bromide, quinones; porphyrins, varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis (dimethylglyoximato)-iron(II) chloride; induline scarlet, neutral red, and substituted derivatives of these compounds.

In another embodiment, the electron transfer moieties are redox proteins. As used herein, a "redox protein" is a protein that binds electrons reversibly. Redox proteins may contain, for example, prosthetic groups, such as flavins or NAD. Proteins such as thioredoxin, which lack prosthetic groups and use, for example, reversible formation of a disulfide bond between two cysteine residues, are also encompassed by the term "redox protein" in the present invention. The flavoprotein phthalate dioxygenase reductase (PDR), a NADH-dependent redox protein, is a preferred electron transfer protein of the present invention (Sevrioukova et al., *Biochemistry* (1996) 35:7058-7068; Gassner, et al., *Biochemistry* (1994) 33:12184-12193; Gassner et al., *Biochemistry* (1995) 34, 13460-13471; and Correll, et al., *Science* (1992) 258:1604-1610). Other non-limiting examples of redox proteins include other flavoprotein reductases, and lactate dehydrogenase.

In another embodiment of the invention, the electron transfer moiety is not a redox protein. In other words, the polypeptide in this embodiment of the invention is not bound or in association with another polypeptide that can undergo electron transfer.

The present invention is directed, in part, to the site selective modification of polypeptides with redox active moieties for preparation of biomaterials capable of long distance electron transfer. In one embodiment, the present invention provides for precise placement of electron transfer donor and acceptor moieties at predetermined sites of an isolated polypeptide that is substantially pure and free of other protein components. The isolated polypeptide is designed in such a way so that the electron donor, primary electron donor, and electron acceptor are held at appropriate distances and orientations for electron transfer between each of the bound electron transfer moieties.

In one embodiment, the polypeptide of the present invention is any polypeptide that can bind at least two electron transfer moieties such that electron transfer occurs between the at least two electron transfer moieties. Such a polypeptide may include, for example a protein composed of helical bundles in a native-like structure with internal cofactor binding sites.

In another aspect of the invention, the polypeptide comprises a four helical bundle scaffold wherein electron transfer moieties are bound between pairs of parallel helices. Such a polypeptide may be designed, for example, using binary patterning of helices with a simple alternating pattern of hydrophilic and hydrophobic helix-forming residues to impose tetramerization via hydrophobic sequestration (Wei, et al., *Protein Science* (2003) 12:92-102; Kamtekar, et al., *Science* (1993) 262, 1680-1685).

In another aspect of the invention, the parallel helices are separated by an amino acid loop sequence. In another aspect of the invention, the loop sequence is rich in glycine and serine amino acid residues.

The invention further provides the following polypeptide sequences, or fragments or variants thereof, and the corresponding polynucleotide sequence encoding these peptides:

| Peptide designation (SEQ ID NO) | Amino acid sequence |
|---|---|
| HH (SEQ ID NO: 1) | GEIWKQHEDALQKFEEALNQFEDLKQLGGSGCGSGG EIWKQHEDALQKFEEALNQFEDLKQLGGSGCGSGG EIWKQHEDALQKFEEALNQFEDLKQLGGSGCGSGG EIWKQHEDALQKFEEALNQFEDLKQL |
| HF (SEQ ID NO: 2) | GSEIWKQHEDALQKFEEALNQFEDLKQLGGSNSGSGG EIWKQHEDALQKFEEALNQFEDLKQLGGSSTGSGG EIWKQFEDALQKFEEALNQFEDLKQLGGSSGSGG EIWKQHEDALQKFEEALNQFEDLKQL |
| 3CB (SEQ ID NO: 3) | GSPQEAQQTAQEAQQALQEHQQAVQAAQQLNELDASQ EHQQATQAAQQTAQKAQQALQKHMATGLYSGSYRSPL VTLWNVAQEAQQALQELQQATQAAQQLNELDALQEHQ QASQAAQQTAQKAQQALQKHQQASQK |
| 3CB2 (SEQ ID NO: 4) | GSPQEAQQTAQEAQQALQEHQQAVQAAQQLNELDASQ EHQQATQAAQQTAQKAQQALQKHMATGGGSGGSPLVT LWNVAQEAQQALQELQQATQAAQQLNELDALQEHQQA SQAAQQTAQKAQQALQKHQQASQK |

In one embodiment of the invention, at least one electron transfer moiety is attached to the polypeptide via a covalent bond. Methods for covalent attachment of small molecules to polypeptides are well known by those of ordinary skill in the art (Dieterich, et al., *Nature Protocols* (2007) 2:532-540). In one aspect of the invention, the electron transfer moiety is attached to the polypeptide via a thioether bond. In another aspect of the invention, the electron transfer moiety is covalently bound using click chemistry (Dieterich, et al., *Nature Protocols* (2007) 2:532-540).

In another embodiment of the invention, the electron transfer moiety is attached to the polypeptide via a metal ligand interaction, as well known in the art. In one embodiment, a metal cofactor is bound to an amino acid side chain of the polypeptide. In another embodiment, the metal site of a metal cofactor complexes with an imidazole nitrogen of a histidine amino acid (Koder, et al., *Dalton Transactions* (2006) 25:3045-3051; Huang, et al., *Proceedings of the National Academy of Sciences of the United States of America* (2004) 101:5536-5541).

In another embodiment, the polypeptide of the present invention can bind at least two electron transfer moieties in such a way so that electron transfer can occur between each of the electron transfer moieties. In this embodiment, the polypeptide provides an edge-to-edge distance between each electron transfer moiety that is preferably in the range of about 0 to about 100 Å. In other embodiments, the preferred edge-to-edge distances between each electron transfer moiety are in the range of about 0 to about 50 Å, more preferably about 1 to about 25 Å, and more preferably about 2 to about 10 Å, with specific distances of about 2, 3, 4, 5, 6, 7, 8, 9, and 10 Å being particularly preferred.

In another embodiment, the polypeptide can bind at least an electron donor, a primary electron donor moiety, and an electron acceptor moiety in such a way so that the primary electron donor is positioned between the electron donor and the electron acceptor, and so that electron transfer can occur between each of the electron transfer moieties. In this embodiment, an edge-to-edge distance between the electron donor and the primary electron donor is in the range of about 0 to about 15 Å, where specific distances of about 1, 2, 3, 4, 5, 6, 7, 8, 9, 10, 11, 12, 13, 14, or 15 Å are preferred, and distances of between about 3, 4, 5, 6, 7 Å are more preferred. Generally, an edge-to-edge distance between the electron donor and primary electron donor of about 5 Å is particularly preferred. In another embodiment, an edge-to-edge distance between the primary electron donor and the electron acceptor is in the range of about 0 to about 15 Å, where specific distances of about 1, 2, 3, 4, 5, 6, 7, 8, 9, 10, 11, 12, 13, 14, or 15 Å is preferred, and distances of about 4, 5, 6, 7, 8, 9, 10, 11, 12 Å are more preferred. Generally, an edge-to-edge distance between the primary electron donor and the electron acceptor of about 8 Å is particularly preferred.

In another embodiment, the edge-to-edge distance between the electron donor and the primary electron donor may be smaller than, equal to, or greater than the distance between the primary electron donor and the electron acceptor.

In another embodiment, electron transfer between the electron transfer moieties is facilitated by modulating the reduction potential of the electron transfer moieties. For example, in one preferred embodiment of the invention, the donor is in a reduced state and the acceptor is in an oxidized state. In another embodiment, the reduction potential of the primary electron donor is higher than the reduction potential of the electron donor, and the reduction potential of the electron acceptor is higher than the reduction potential of the primary electron donor. In anther embodiment, the donor cofactor has a lower reduction potential than the acceptor. In another preferred embodiment, the difference in net reduction potential between the electron transfer moieties is in the range of about 0 to about 5 V, where a reduction potential difference of about 0 to about 2V is preferred, and a range of about 0.015 and about 1 V is more preferred, and specific reduction potential differences of about 0.01, 0.05, 0.1, 0.2, 0.3, 0.4, and 0.5 V are particularly preferred.

In another aspect of the invention, the electron transfer moieties are arranged in a charge separated state. In another aspect, the charge separated state comprises a cationic electron donor and an anionic electron acceptor. In yet another aspect of the invention, the anionic and cationic charges are separated over a distance within the range of about 0 to about 50 Å, where a range of about 5 to about 40 Å is preferred, more preferably about 10 to about 30 Å, and still more preferably about 15 to about 25 Å. Specific preferred charge separation ranges include about 15, 16, 17, 18, 19, 20, 21, 22, 23, 24, and 25 Å. In another embodiment the charge separation distance may be at least about 15, 16, 17, 18, 19, 20, 21, 22, 23, 24, or 25 Å.

In another aspect of the invention, the electron transfer is vectorial electron transfer, that is, electron transfer that occurs in a directional fashion. For example, in one aspect of the invention, an electron may propagate from a primary electron donor to a first electron acceptor and then to a second electron acceptor in an extended electron transfer chain.

In another aspect of the invention, electron transfer is initiated when a primary electron donor is excited by light, such as, for example infrared, ultraviolet, and visible light. Selection of the appropriate wavelength for electron excitation is governed by the specific primary electron donor, and can be easily determined by the skilled artisan. For example, ZnPC can be excited at about 675 nm (FIG. 7), Zn-hemin can be excited at about 430 nm, Zn-chlorin can be excited at about 645 nm, and Zn-naphthocyanine can be excited at about 775 nm.

In an alternate embodiment, electron transfer between the electron transfer moieties can be indirect, utilizing electron transfer mediators which are free in solution or imbedded in a matrix. For example, an electron transfer mediator used in the present invention may include, but is not limited to, ethylenediaminetetraacetic acid (EDTA), methyl viologen, and benzylviologen.

In another embodiment, electron transfer is initiated by attachment of the polypeptide to a solid support such as an electrode. In one embodiment, the electrode serves as either an electron donor or acceptor. Electrode attachment allows for electron transfer via an applied potential for electronic methods or electron transfer monitoring.

In another aspect of the invention, the polypeptide assembly is further attached to at least one electrode to create photovoltaic cells. In another aspect of the invention, the polypeptide assembly is placed in membranes. In yet another aspect of the invention, the polypeptide assembly is used to drive redox reactions such as the hydrolysis of water.

An exemplary polypeptide assembly of the present invention is depicted in FIG. 1. As shown in FIG. 1, the inventive polypeptide may comprise PDR flavin domain that is fused to a polypeptide charge separation domain, where a first electron donor (D1), a primary donor (PD), a first electron acceptor (A1), and a second electron acceptor (A2) are positioned in the charge separation domain in such a way as to enable electron transfer between the electron transfer moieties. The charge separation domain may be configured as a 4-helix polypeptide bundle of two parallel alpha helical domains that are joined via a disulfide bond linkage. The charge separation domain is covalently bound to a PDR flavin domain on the donor end of the charge separation polypeptide.

Figure 2:
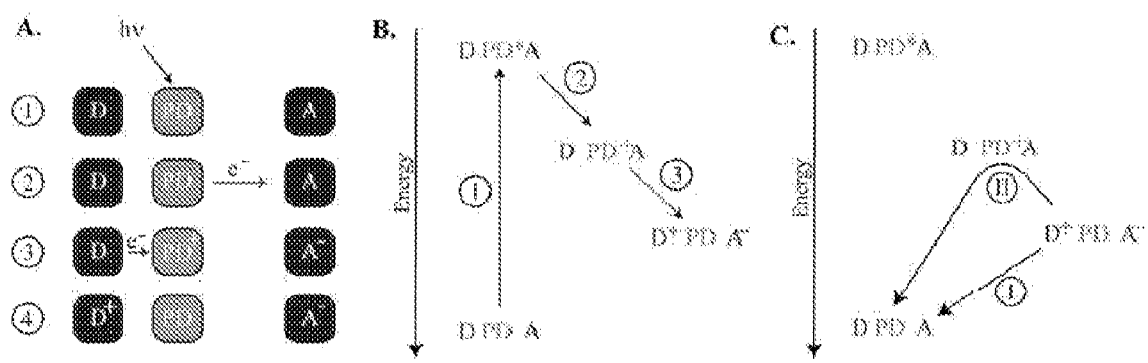
FIGS. 2A-2C illustrate the stepwise mechanism (FIG. 2A) and energy level diagram (FIG. 2B) of a three-component charge separation device, and principle relaxation pathways of the charge separation state (FIG. 2C).

Without being bound by any particular theory or mechanism of the invention, a mechanism for electron transfer in a three component charge separation device is shown in FIG. 2A-2C. Upon photoexcitation, the primary donor transfers and electron to the first acceptor molecule. Before unproductive charge recombination via back electron transfer can occur, the donor transfers an electron to the primary donor, blocking the back reaction (FIG. 2A and FIG. 2B). Thus the electron that was transported to the first electron acceptor is free to propagate down the electron transfer chain to the second electron acceptor, as illustrated in FIG. 1.

The fully charge-separated state principally relaxes back to the ground state by one of the two mechanisms presented in FIG. 2C. The charge separated state can either undergo direct long range tunneling between the donor and acceptor molecules (arrow (I) in FIG. 2C), or a two step recombination process can occur, where an equilibration between the charge separated state and the D $PD^+$ $A^-$ intermediate occurs followed by tunneling from the acceptor to the ground state. This alternate mechanism is illustrated by arrow (II) in FIG. 2C.

The following examples serve to more fully describe the manner of using the above-described invention, as well as to set forth the best modes contemplated for carrying out various aspects of the invention. It is understood that these examples in no way serve to limit the true scope of the invention, but rather are presented for illustrative purposes.

EXAMPLES

Example 1

Preparation Cofactor-Binding Precursor Polypeptides

In this example, the following series of cofactor-bonding polypeptides was prepared:

| Peptide designation (SEQ ID NO) | Amino acid sequence* |
|---|---|
| HP-1 (SEQ ID NO: 5) | CGGG<u>EIWKQHEEALKKFEEALKQFEELKKL</u> |
| HP-6 (SEQ ID NO: 6) | CGGG<u>EIWKQHEDALQKFEEALNQFEDLKQL</u> |
| HP-7 (SEQ ID NO: 7) | <u>GEIWKQHEDALQKFEEALNQFEDLKQL</u>GGSGCGSGG <u>EIWKQHEDALQKFEEALNQFEDLKQL</u> |

*helical portions of the polypeptides are underlined

Peptide synthesis reagents were purchased from PerSeptive Biosystems (Foster City, Calif.). Solid phase peptide synthesis was performed on a continuous flow PerSeptive Biosystems (Framingham, Mass.) peptide synthesizer as described (Fuziwara, et al., *Journal Of Inorganic Biochemistry* (2002) 91:515-526; Choma, et al., *Journal of the American Chemical Society* (1994) 116:856-865). Crude peptides were purified to homogeneity by reversed phase $C_{18}$ HPLC with aqueous-acetonitrile gradients containing 0.1% (vol/vol) trifluoroacetic acid.

HP-1 (SEQ ID NO: 5), the first polypeptide in the series, was rationally designed using the principles of binary patterning, with the ligand histidines placed at internal positions between helical pairs to form the binding site (Huang, et al., *Proceedings of the National Academy of Sciences of the United States of America* (2004) 101:5536-5541). In short, the HP-1 (SEQ ID NO: 5) peptide structure was based on the x-ray crystal structure of the apomaquette L31M, derived from the structurally heterogeneous tetraheme-binding H10H24 prototype. Heme insertion was modeled with angular constraints statistically derived from natural proteins, and the pattern of hydrophobic and hydrophilic residues on each helix was altered to account for structural reorganization (Huang, et al., *Proceedings of the National Academy of Sciences of the United States of America* (2004) 101:5536-5541).

The HP-1 (SEQ ID NO: 5) helical sequence was then modified in a stepwise manner to enable structural analysis by introducing amino acid resides known to increase NMR chemical shift dispersion. The resulting protein was homotetrameric polypeptide HP-6 (SEQ ID NO: 6).

The HP-6 (SEQ ID NO: 6) polypeptide was modified to include a connectivity sequence to afford the homodimeric helix-loop-helix variant HP-7 (SEQ ID NO: 7). HP-7 (SEQ ID NO: 7) was prepared by recombinant expression in isotopically labeled in *E. coli* as a fusion protein with a TEV protease cleavage site.

It is observed that two HP-7 (SEQ ID NO: 7) polypeptides can dimerize to form a HP-7:HP-7 4-helical bundle (FIG. 3A-3C). The HP-6 peptide (SEQ ID NO: 6), and other peptides described herein which contain two helical domains also dimerize to form 4-helical structures. The dimerized peptides may be connected via, for example covalent attachment using a disulfide bond, to form a single 4-helical polypeptide.

Figure 3:
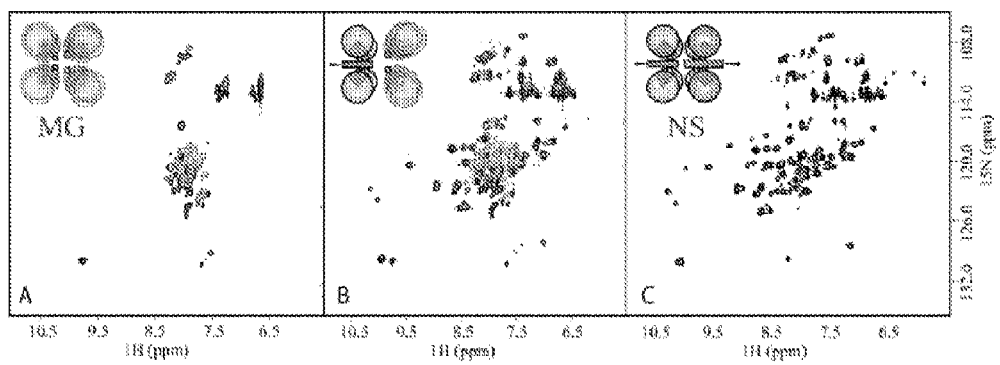
FIGS. 3A-3C illustrate NMR spectra of a de novo designed HP-7 (SEQ ID NO: 7) 4-helical bundle polypeptide in a molten globule (MG) (FIG. 3A), single heme-bound panel (FIG. 3B) and native-like (NS) state (FIG. 3C).

Characterization of HP-7 (SEQ ID NO: 7) by NMR demonstrates a stepwise molten globule to native-like transitioning in this protein, where the structure of each helix in the polypeptide that donates a ligand to the heme cofactor was found to exhibit native-like motif. As shown in FIG. 3, prior to cofactor binding, the HP-7 (SEQ ID NO: 7) polypeptide is a molten globule protein, as evidenced by the lack of chemical shift dispersion in the N HSQC spectrum (FIG. 3A). When one equivalent of heme is added, two of the helical domains of the polypeptide transition to a native-like state, while the remaining two unligated helices remain in the molten globule form (FIG. 3B). Upon addition of the second heme equivalent, HP-7 (SEQ ID NO: 7) transitions to a 4-helical bundle native-like structure.

The native-state motif transition is also observed when the HP-7 (SEQ ID NO: 7) polypeptide is coordinated to other structurally distinct cofactors such as tetraphenylporphyrins, bacteriochlorophylls and Heme A (Koder, et al., *Journal of the American Chemical Society* (2006) 128:14450-14451).

In spite of the structural disparity between the HP-1 (SEQ ID NO: 5) and HP-7 (SEQ ID NO: 7) polypeptides, where over 40% of the helical residues were mutated on the polypeptide surface, each peptide exhibits the same molten globule-to-native-like structural transition upon the addition of a cofactor.

These data demonstrate that binary patterning coupled with appropriate positioning of ligand residues, allows for creation of a native-like structure in proteins with bound cofactors. As demonstrated below, the HP-7 (SEQ ID NO: 7) polypeptide may serve as a precursor for a charge-separation domain of the present invention.

Example 2

Modulating Cofactor Redox Potential

In Example 2, the reduction potential of the peptides prepared in Example 1 is regulated by modulation of peptide ionic charge and cofactor structure. The net charge of the polypeptides is calculated using conventional methods known in the art.

Modification of surface amino acid residues in HP-1 (SEQ ID NO: 5) to afford the HP-7 (SEQ ID NO: 7) polypeptide produces an increase in anionic character of the polypeptide. In particular, HP-1 (SEQ ID NO: 5) exhibits a near neutral net charge whereas HP-7 (SEQ ID NO: 7) is highly anionic. At pH 7, the calculated net charge of the HP-7 (SEQ ID NO: 7) homodimer is –15.6.

Such a change in ionic character of the polypeptides influences the reduction potential of bound cofactors. For example, in earlier experiments, HP-7 heme complex exhibits a reduction potential that was 45 mV more positive than the reduction potential of the HP-1-heme complex.

Specific Glu→Ala mutations in the HP-7 peptide produce an alternate peptide referred to here as CC-9 (SEQ ID NO: 8). The CC-9 peptide shown in the table below:

| Peptide designation (SEQ ID NO) | Amino acid sequence* |
|---|---|
| HP-7 (SEQ ID NO: 7) | <u>GEIWKQHEDALQKFEEALNQFEDLKQL</u>GGSGCGSGG <u>EIWKQHEDALQKFEEALNQFEDLKQL</u> |
| CC-9 (SEQ ID NO: 8) | <u>GEIWKQHEDALQKFEEALNQFEDLKQL</u>GGSGCGSGG <u>EIWKQHADALQKFAEALNQFADLKQL</u> |

*Glu→Ala mutations are indicated in grey; helical portions of the polypeptides are underlined The three anionic glutamate residues in HP-7 (SEQ ID NO: 7) that were targeted for alanine substitution were predicted to buried in the hydrophobic core of the polypeptide (Huang, et al., *Proceedings of the National Academy of Sciences of the United States of America* (2004) 101:5536-5541).

The CC-9 (SEQ ID NO: 9) polypeptide exhibits a 101 mV increase in bound heme reduction potential compared to the HP-7 (SEQ ID NO: 7) polypeptide. These data are shown in FIG. 4B.

Figure 4:
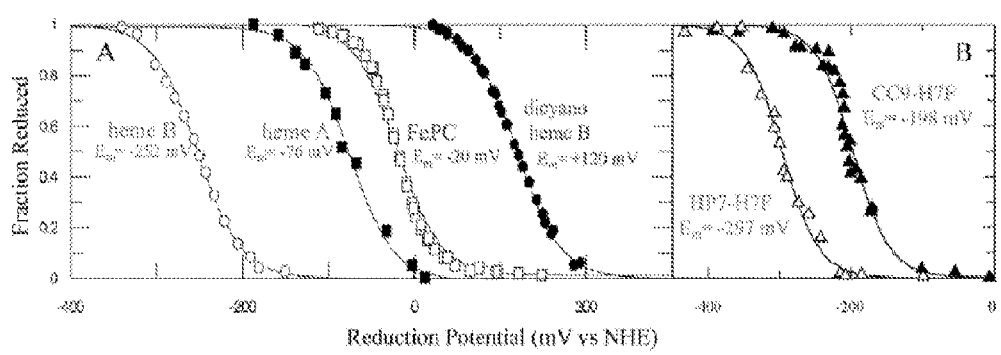
FIGS. 4A-4B illustrate a series reduction potential vs. native hydrogen electrode plots for various ferric cofactors bound via bis-histidine ligation to the polypeptide HP-1 (SEQ ID NO: 5) (FIG. 4A). Electrostatic-mediated modulation of reduction potential of HP-7-H7F and CC-9-HF-7 polypeptides is depicted (FIG. 4B).

Further, as demonstrated in FIG. 4A, the reduction potential of the polypeptide system can also be controlled using the cofactor alone. Three distinct ferric cofactors bound via a bis-histidine ligation to HP-1 (SEQ ID NO: 5) exhibited a reduction potential difference spanning approximately 400 mV.

These data demonstrate cofactor reduction potential is effectively modulated by the cofactor identity and by regulation of amino acid electrostatics.

Example 3

Optimizing Cofactor Binding Affinity

This example describes an investigation of the rotameric distribution of heme-bound histidine side chains for isolation of rotamer-dependent helical sequence preferences which provide optimal side chain-cofactor packing interactions for each rotamer. The optimal sequence templates predict high-affinity porphyrin binding sites in the inventive helical polypeptides.

A highly nonredundant subset of the protein databank is analyzed to determine a rotamer distribution for helical histidines bound to heme cofactors. Analysis of the entire nonredundant database for helical sequence preferences near the ligand histidine demonstrates little preference for amino acid side chain identity, size, or charge (Cowley, et al., *Inorganic Chemistry* (2006) 45:9985-10001). However, when the database is subdivided by ligand histidine rotamer, a strong preference for the following consensus sequence is revealed:

```
                                    (SEQ ID NO: 9)
IXXXLXXHAXXAIIIF.
```

The HP-7 polypeptide (SEQ ID NO: 7) from Example 1 is modified to incorporate the preferred consensus sequence to produce a polypeptide referred to herein as CC-10 (SEQ ID NO: 10). An additional polypeptide designated "H7F" (SEQ ID NO: 11) is prepared, based on a His$_7$→Phe mutation of the HP-7 (SEQ ID NO: 7) polypeptide. The structure for these peptides are shown below:

| Peptide designation (SEQ ID NO) | Amino acid sequence* |
|---|---|
| HP-7 (SEQ ID NO: 7) | GEIWKQHEDALQKFEEALNQFEDLKQLGGSGCGSGG EIWKQHEDALQKFEEALNQFEDLKQL |
| CC-10 (SEQ ID NO: 10) | GEIWKQHEDALQKFEEALNQFEDLKQLGGSGCGSGG EILKQHADAAQKIFEALNQFEDLKQL |
| H7F (SEQ ID NO: 11) | GEIWKQHEDALQKFEEALNQFEDLKQLGGSGCGSGG EIWKQFEDALQKFEEALNQFEDLKQL |

Figure 5:
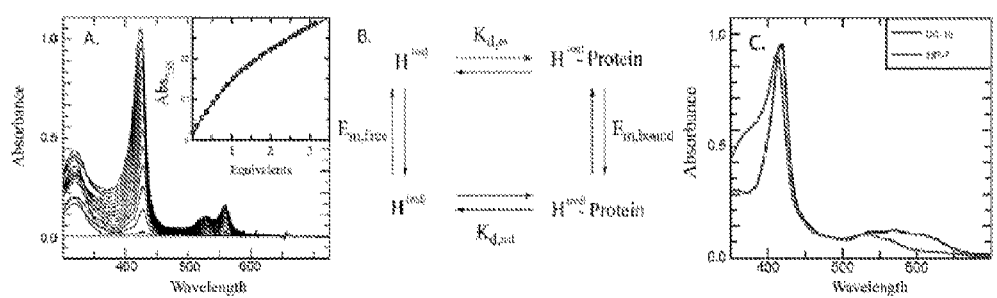
FIGS. 5A-5C depict measurements of heme affinity to HP-7 (SEQ ID NO: 7) and CC-10 (SEQ ID NO: 10) polypeptides. Determination of the heme affinity in the reduced state is described in FIG. 5A, a model depicting the coupling between heme oxidation state and binding is depicted in FIG. 5B, and an absorption spectra of equimolar HP-7 (SEQ ID NO: 7) and CC-10 (SEQ ID NO: 10) heme complexes aged for one week at 4° C. is depicted in FIG. 5C.

*Mutated amino acids are indicated in grey; helical portions of the polypeptides are underlined As shown in FIG. 5, the binding affinities of heme for the HP-7 (SEQ ID NO: 7) and CC-10 (SEQ ID NO: 10) polypeptides may be determined by titration of reduced heme into an anaerobic protein solution poised at <−400 mV vs. the normal hydrogen electrode. The reduced heme binding constants are also measured for His$_{42}$→Phe mutants of the polypeptides. Oxidized heme exhibits a 220 pM binding constant for the HP-7 (SEQ ID NO: 7) peptide and a 10.7 pM affinity for the CC-10 peptide (SEQ ID NO: 10). Analysis of the absorption spectra of equimolar HP-7 (SEQ ID NO: 7) and CC-10 (SEQ ID NO: 10) heme-bound complexes aged for one week at 4° C. reveals a long-term stability of the CC-10 (SEQ ID NO: 10) polypeptide compared with the HP-7 polypeptide. These data demonstrate that high cofactor affinity contributes to long term stability of the cofactor-polypeptide constructs.

Figure 6:
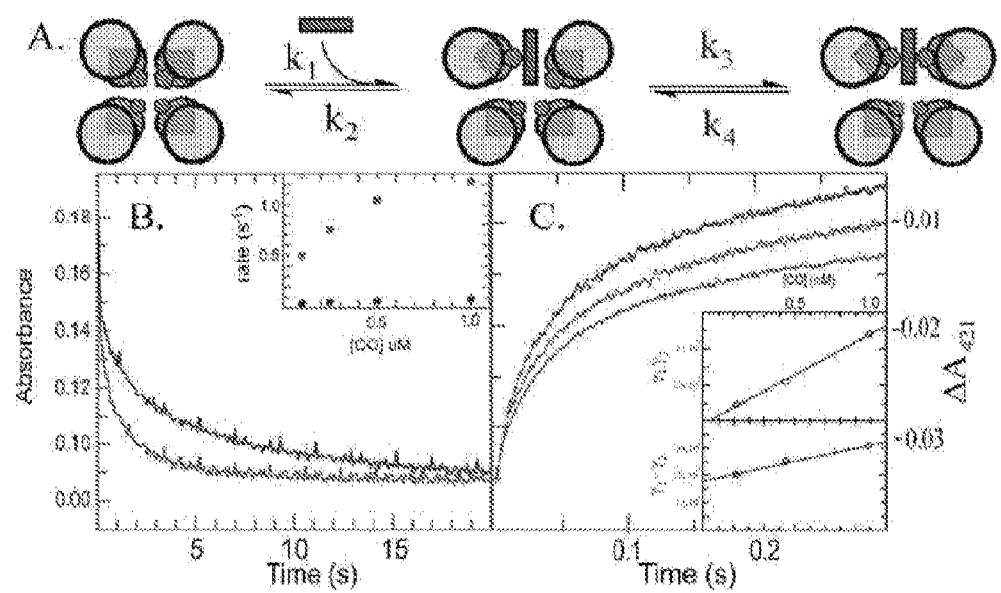
FIGS. 6A-6C illustrate two stage heme binding to HP-7 (SEQ ID NO: 7) and CC-10 (SEQ ID NO: 10) polypeptides. A model of stepwise binding is illustrated in FIG. 6A.

While the present invention is not limited to any particular theory or mechanism of action, it is noted that heme binding can be modeled as a two step process, as illustrated in FIG. 6 where the heme first binds in a pentacoordinate manner and then the second histidine ligand binds to the cofactor (FIG. 6A). The rate constant of the second step ($k_3$) was calculated to quantitate the distal histidine coordination equilibrium (FIG. 6). The histidine off rate ($k_4$) is estimated by limiting the rate of carbon monoxide binding to the ferrous protein complex at high carbon monoxide concentrations (FIG. 6B). The HP-7:H7F peptide is thus calculated to have a limiting value of 1.4 s$^{-1}$, whereas the CC-10:H7F dimer is found to be 15 fold slower at 0.09 s$^{-1}$. The histidine off-rate ($k_4$), i.e., the rate at which histidine dissociates from the polypeptide, was determined by performing the CO-ferrous heme complex and flashing the ligand off with light. Analysis of the rebinding kinetics using the method described by Hargrove et al. (Hargrove et al., *Biophysical Journal* (2000) 79:2733-2738; Kundu, et al., *Proteins-Structure Function And Genetics* (2003) 50:239-248) demonstrated that CC-10:H7F has a histidine on-rate that is 3-fold faster than HP-7:H7F.

Example 4

Construction of Two-Cofactor "HF" Binding Polypeptide

In this example, a two-cofactor binding protein with one bis-histidine heme binding site and one mono-histidine ZnPC binding site is prepared. In particular, a four-helix single-chain polypeptide designated "HF" (SEQ ID NO: 2) was constructed by connecting the gene for CC-10 (SEQ ID NO: 10) to the gene for His7→Phe CC-10 mutant separated with a GGSGSGSGG (SEQ ID NO: 17) connecting loop. The full sequence of the HF polypeptide (SEQ ID NO: 2) is provided below:

| Peptide designation (SEQ ID NO) | Amino acid sequence* |
|---|---|
| HF (SEQ ID NO: 2) | GEIWKQHEDALQKFEEALNQFEDLKQLGGSGCGSGG EILKQHADAAQKIFEALNQFEDLKQL GGSGSGSGG GEIWKQFEDALQKFEEALNQFEDLKQLGGSGCGSGG EILKQHADAAQKIFEALNQFEDLKQL |

*Helical portions of the polypeptide are underlined

Figure 7:
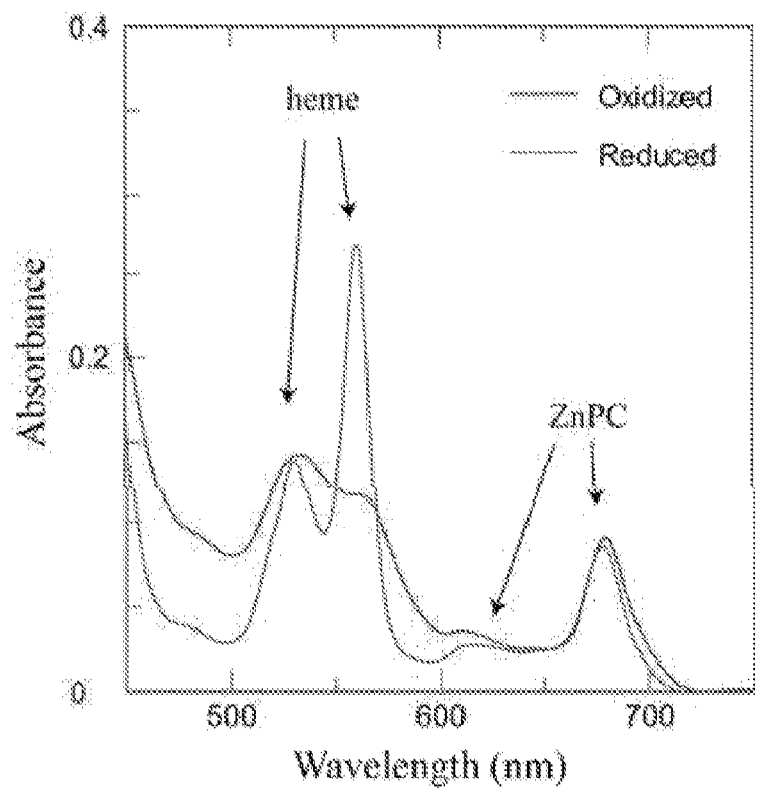
FIG. 7 illustrates oxidized and reduced B- and Q-band absorbance spectra of the heme-ZnPC heterocomplex of HF (SEQ ID NO: 2).

HF (SEQ ID NO: 2) exhibits a high binding affinity for one equivalent of heme one equivalent of ZnPC, which is subsequently introduced as a concentrated solution in DMSO. An NMR spectrum of the resulting heterocomplex demonstrates formation of a native-like polypeptide structure. An absorbance spectra of a ZnPC:heme:HF heterocomplex is shown in FIG. 7. Complex structure analysis by magnetic circular dichroism confirms that the ZnPC cofactor binds to each polypeptide in a mono-histidine coordination. These data demonstrate successful utilization of de novo protein design to create a matrix which can complex a phthalocyanine in 'splendid isolation' without the need for complicated calculation or molecular modeling.

Example 5

Preparation of Reductase Domain for Conjugation to Polypeptide Construct

Figure 8:
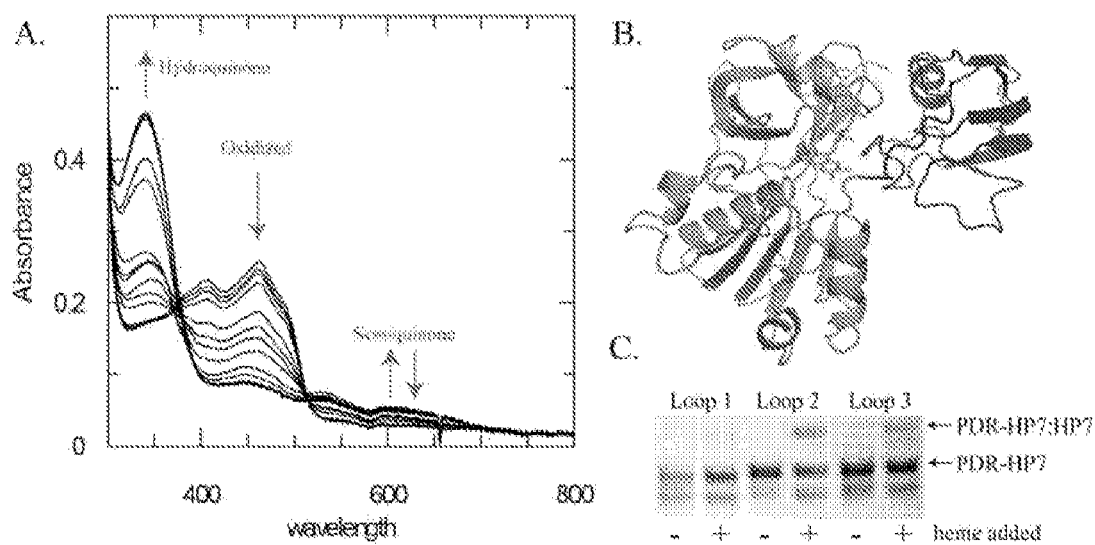
FIG. 8A illustrates anaerobic NADH titration of recombinant PDR expressed without the Reiske iron-sulfur domain. The domain structure of PDR is shown in FIG. 8B, and screening of the optimal connecting loop length for covalent dimerization of PDR and HP-7 (SEQ ID NO: 7) polypeptide is illustrated in FIG. 8C.

In this Example, a protein construct of the phthalate dioxygenase reductase (PDR) flavin domain is prepared for conjugation to the inventive polypeptide assembly. A truncated form of PDR, illustrated in FIG. 8, is engineered to produce a gene which lacks the iron-sulfur domain to create a TEV protease-cleavable His$_6$ tagged construct. The PDR construct was expressed, purified and cleaved using standard methods to produce a folded flavoprotein capable of reacting with NADH. Such a construct may be fused to the polypeptide electron transfer domain of the present invention.

Example 6

Identification of an Optimal Loop Sequence for PDR-HP-7 Polypeptide Assembly A short peptide loop sequence for appending a PDR moiety to an electron transfer polypeptide assembly of the present invention is described. The loop sequence is designed to minimize the distance between the PDR and electron transfer polypeptide moiety and to maintain the structure and function of the connected domains.

A single HP-7 (SEQ ID NO: 7) polypeptide monomer is fused to the PDR domain using the variable peptide loop sequences identified below:

| Peptide designation (SEQ ID NO) | Variable loop sequence |
|---|---|
| Loop 1 (SEQ ID NO: 12) | GATNGG |
| Loop 2 (SEQ ID NO: 13) | GATNTNGG |
| Loop 3 (SEQ ID NO: 14) | GATNTNARGG |

PDR-HP-7 chimeras connected by the variable peptide loop sequences are mixed with free HP-7 (SEQ ID NO: 7). The ferric heme cofactor is then added to promote cofactor-mediated binding of the PDR-HP-7 construct with the free HP-7 (SEQ ID NO: 7) to produce a two-cofactor PDR-HP-7:HP-7 assembly. A native gel is run to screen for heterodimer assembly in the presence and absence of the cofactor. As illustrated in FIG. 8C, the PDR-HP7 construct prepared with the Loop 2 (SEQ ID NO: 13) sequence affords the highest concentration of the PDR-HP7:HP7 heterocomplex. Accordingly, Loop 2 (SEQ ID NO: 13) is identified here as an optimal loop length.

Example 7

Optimization of Electron Transfer in Two-Cofactor "HF" Polypeptide Domain

The initial electron transfer step of the "HF" (SEQ ID NO: 2) polypeptide described in Example 4 is examined in this example. As described above, the HF (SEQ ID NO: 2) polypeptide is designed to bind a zinc(II)-phthalocyanine (ZnPC) primary donor and a heme acceptor cofactor. The two cofactors are held in this polypeptide at an edge-to-edge distance of about 8 Å.

Electron transfer rates and yields are measured by time resolved absorption spectroscopy with a Johnson Foundation spectrometer using well established techniques (Li et al., *Biochemistry* (1998) 37:2818-2829; Li, et al., *Biochemistry* (2000) 39:7445-7454; Li, et al., *Photosynthesis Res.* (2000) 64:41-52; Xu, et al., *J. Phys. Chem. B* (2000) 104:8035-8043; Xu, et al., *Biochemistry* (2002) 41:10021-10025; Madeo, et al., *Biochemistry* (2005) 44:10994-11004). A 10 ns Nd:YAG laser (Continuum Surelite 2) is used to provide the actinic flash. Frequency doubling allowed for excitation at 532 nm, which is near the absorbance max of the bound ZnPC B-band. Reactions are followed using a continuous Quartz-Tungsten-Halogen measuring lamp from 390 to 1000 nm, 50 ns to 100 s, and 275 to 340 K, and single wavelength studies are centered at the reduced Soret peak maximum (421 nm) and the oxidized Soret maximum (421 nm) for the heme cofactor. The delay time between the actinic and probing light is controlled with a digital time delay/pulse generator (Stanford Research system, DG535) and the system is capable of determining lifetimes ≥0.1 μs. For examining reactions at temperatures above 0° C. a jacketed cuvette is attached to a circulating water bath.

Since phthalocyanines suffer from oxygen quenching (Ogunsipe, et al., *New J. Chem.* (2004) 28:822-827), the above experiments are performed anaerobically in special glassware (Dutton, et al., *Methods in Enzymology* (1978) 54:411-435) with solutions that are initially degassed by repeated cycles of vacuum evacuation and flushing with argon. Residual oxygen is removed by the addition of glucose, glucose oxidase and catalase (Berg, et al., *Biochemistry* (1980) 19:3186-3189).

Prophetic Example 1

Construction of Three-Cofactor Polypeptide Domain

As described above, the HF polypeptide (SEQ ID NO: 2) is capable of binding a ZnPC primary donor and a heme acceptor cofactor. The HF polypeptide (SEQ ID NO: 2) may additionally be combined with a covalently attached "C-type heme" as an electron transfer donor, resulting in a three cofactor helical bundle where the three polypeptide binding sites target a specific cofactor using a distinct binding mechanism.

In order to add a third heme molecule to the polypeptide assembly, each helix of the HF polypeptide (SEQ ID NO: 2) may be extended by specific amino acids which provide addition of a bis-histidine binding site for the third cofactor which is bound between diagonal helices rather than by adjacent helices. (Ghirlanda, et al., *Journal of the American Chemical Society* (2004) 126:8141-8147) A model of this protein will be created computationally which is comprised only of the helical backbone atoms, and amino acid side chains will be selected according to the principles of binary patterning, with hydrophobic residues placed into the protein core and hydrophilic residues placed at surface-exposed sites. A heme cofactor can then be covalently attached to the new bis-histidine binding site.

The third cofactor may be attached to the new binding site by covalent attachment in vivo during protein expression. For example, in vivo C-heme attachment can be carried out by co-transfecting expression bacteria with pEC86, a plasmid which contains the entire *E. coli* cytochrome C maturation apparatus (Arslan et al., *Biochemical And Biophysical Research Communications* (1998) 251:744-747). The domain may be cloned into the pMAL-p2 vector (New England Biolabs), which can express the domain as a fusion with maltose binding protein containing a periplasmic targeting tag. The target protein can then be isolated using standard methods.

One possible sequence for the third cofactor binding site is "AXXACXACHXXLA" (SEQ ID NO: 15) which contains a "CXXCH" (SEQ ID NO: 16) recognition sequence (where X is any amino acid) recognized by the cytochrome C maturation apparatus. Another helix from which the distal histidine will originate, may retain the optimized CC-10 (SEQ ID NO: 10) polypeptide sequence. Remaining residues can be selected using binary patterning and the above-described heme binding site analysis, in combination with conventional knowledge of the bicomplex structure. Cofactor binding, structural specificity, and complex stability can be assessed using the methods described above (Wei, et al., *Protein Science* (2003) 12:92-102; Kamtekar, et al., *Science* (1993) 262, 1680-1685).

Prophetic Example 2

Conjugation of PDR to Three-Cofactor Polypeptide Domain

A three cofactor polypeptide prepared as described in Prophetic Example 1 can be fused to a PDR domain to provide efficient vectorial electron transfer. For example, the three-cofactor system prepared as described in Example 8 can be attached to the PDR construct of Example 5 using the optimized loop sequence described in Example 6 by ligation-independent cloning (Chiu et al., (2004) *Nucleic Acids Research* 32).

Such a fused construct can be examined using anaerobic equilibrium NADH titrations (Koder, et al., *Biochemistry* (2002) 41:14197-14205). In short, concentrated NADH solutions may be anaerobically titrated into a 20-30 µM solution of the construct. The construct can initially be loaded with heme B at the acceptor site. The stoichiometry of heme and flavin reduction as a function of the amount of added NADH can be assessed spectrophotometrically. Formed constructs can then be examined using stopped-flow kinetic analysis.

Prophetic Example 3

Measuring Charge Separation in PDR-Polypeptide Assembly

Light driven directional electron transfer of a PDR-polypeptide assembly can be measured by flash spectroscopic analysis. In equilibrium anaerobic titrations, a PDR-polypeptide construct of the invention will only reduce the heme cofactor proximal to the PDR domain, resulting in a visible spectrum showing the flavin mononucleotide semiquinone radical, one reduced heme and one oxidized heme, along with the ZnPC B band spectra. Light filtered to >600 nm may be directed into a cuvette containing a solution of the construct using a fiber optic cable, and time-dependence of the appearance of a second reduced heme, follow by re-reduction of the flavin mononucleotide with excess solution NADH, assessed spectrophotometrically.

The system may be further analyzed by time-resolved absorption spectroscopy. Such experiments allow for determination of electron transfer rates for two electron transfers: the electron transfer from the flavin semiquinone to the proximal heme, and the re-reduction of the phthalate dioxygenase reductase flavin cofactor by solution NADH.

Prophetic Example 4

Extending the Charge Separation of PDR-Polypeptide Assembly

The charge separation distance, i.e., the distance between an cationic electron transfer moiety and an anionic electron acceptor moiety, can be extended to at least 30 Å to provide a prolonged charge separation lifetime by adding a second electron acceptor moiety to the acceptor side of the polypeptide assembly described in Prophetic Example 2. Each helix can be extended by three heptads to accommodate an additional cofactor binding site. For example, a bis-histidine binding site can be added at a 10 Å distance from the first electron acceptor in the assembly. Such a construct can be recombinantly expressed, purified, and assembled as described above. Structural characterization can be achieved by NMR spectroscopy.

The invention claimed is:

1. A construct comprising an isolated polypeptide and at least three electron transfer moieties bound to said polypeptide such that electron transfer can occur between each of the electron transfer moieties, wherein the electron transfer moieties include at least an electron donor, a primary electron donor, and an electron acceptor and wherein the edge-to-edge distance between each electron transfer moiety is in the range of 1 to 25 Å, and wherein the edge-to-edge distance between the electron donor and the primary electron donor is smaller than the distance between the primary electron donor and the electron acceptor.

2. The construct according to claim 1, wherein the primary electron donor binds to said polypeptide such that such that it is positioned between the electron donor and the electron acceptor.

3. The construct according to claim 1, wherein an electron is transferred from the primary electron donor to the electron acceptor.

4. The construct according to claim 1, wherein an electron is transferred from the electron donor to the primary electron donor.

5. The construct according to claim 1, wherein the primary electron donor transfers an electron when excited by light.

6. The construct according to claim 1, wherein the electron is transferred from the electron donor to the primary electron donor after transfer of an electron from the primary electron acceptor.

7. The construct according to claim 1, wherein the edge-to-edge distance between the electron donor and the primary electron donor is 5 Å, and the edge-to-edge distance between the primary electron donor and the electron acceptor is 8 Å.

8. The construct according to claim 1, wherein the reduction potential of the primary electron donor is higher than the reduction potential of the electron donor, and wherein the reduction potential of the electron acceptor is higher than the reduction potential of the primary electron donor.

9. The construct according to claim 1, wherein the polypeptide contains at least one helical domain.

10. The construct according to claim 1, wherein at least one electron transfer moiety is bound to the polypeptide via a covalent bond.

11. The construct according to claim 1, wherein at least one electron transfer moiety is bound to an amino acid side chain of the polypeptide via a transition metal-ligand complex interaction.

12. The construct according to claim 11, wherein the amino acid is a histidine residue.

13. The construct according to claim 1, further comprising at least one additional polypeptide linked to said isolated polypeptide.

14. The construct according to claim 13, wherein the at least one additional polypeptide is flavoprotein reductase.

15. The construct according to claim 1, wherein the polypeptide comprises the amino acid sequence of SEQ ID NO: 3.

16. The construct according to claim 1, wherein the polypeptide comprises the amino acid sequence of SEQ ID NO: 4.

17. The construct according to claim 1, wherein the electron transfer is vectorial electron transfer.

18. The construct according to claim 1, wherein the electron transfer moieties are arranged in a charge separated state comprising a cationic electron donor and an anionic electron acceptor.

19. The construct according to claim 1, wherein the anionic and cationic charges are separated over a distance of at least 20 Å.

20. The construct according to claim 18, wherein the lifetime of the charge separated state is at least 0.1 nanoseconds.

21. The construct according to claim 1, wherein at least one electron transfer moiety is a transition metal complex.

22. The construct according to claim 21, wherein the transition metal complex comprises zinc, ruthenium, rhenium, osmium, platinum, copper, or iron.

23. The construct according to claim 1, wherein at least one electron transfer moiety is an organic electron donor or acceptor.

24. The construct according to claim 1, wherein at least one electron transfer moiety is an electrode.

25. The construct according to claim 1, wherein at least one electron transfer moiety is zinc(II)phthalocyanine.

26. The construct according to claim 1, wherein at least one electron transfer moiety is an iron porphyrin.

27. A photovoltaic assembly comprising a charge separation domain covalently linked to a matrix, wherein the charge separation domain comprises a construct according to claim 1.

28. The photovoltaic assembly according to claim 27, wherein the matrix is an electrode.

* * * * *